United States Patent [19]

Berg et al.

[11] Patent Number: 5,139,502

[45] Date of Patent: Aug. 18, 1992

[54] DRAINAGE TUBE FOR SINUS MAXILLARIS, A MEANS FOR ITS INSERTION AND A MEANS FOR MAKING A HOLE FOR ITS POSITIONING

[75] Inventors: Olle Berg, Lidingö ; Lars Lejdeborn, Vällingby, both of Sweden

[73] Assignee: Atos Medical AB, Horby, Sweden

[21] Appl. No.: 465,122

[22] PCT Filed: Aug. 19, 1987

[86] PCT No.: PCT/SE87/00364

§ 371 Date: Mar. 26, 1990

§ 102(e) Date: Mar. 26, 1990

[87] PCT Pub. No.: WO89/01350

PCT Pub. Date: Feb. 23, 1989

[51] Int. Cl.$^5$ .............................. A61M 25/01
[52] U.S. Cl. ............................ 606/108; 604/8; 604/264
[58] Field of Search ............ 604/8, 11, 15, 264, 604/285; 606/79, 80, 108–109, 167, 170, 180, 184

[56] References Cited

U.S. PATENT DOCUMENTS

| | | |
|---|---|---|
| 1,123,730 | 1/1915 | Greenfield ............ 606/170 X |
| 2,452,813 | 11/1948 | Wade . |
| 3,807,409 | 4/1974 | Paparella et al. . |
| 3,871,380 | 3/1975 | Heros . |
| 3,948,271 | 4/1976 | Akiyama ............ 606/109 X |
| 3,982,545 | 9/1976 | Silverstein . |
| 4,015,607 | 4/1977 | Wright, III . |
| 4,623,348 | 11/1986 | Feit ............ 604/264 |
| 4,649,918 | 3/1987 | Pegg et al. ............ 606/79 |
| 4,695,275 | 9/1987 | Bruce et al. ............ 604/264 |
| 4,696,308 | 9/1987 | Meller et al. ............ 606/180 X |
| 4,913,143 | 4/1990 | Oloff et al. ............ 606/170 |
| 4,964,850 | 10/1990 | Bouton et al. ............ 606/108 |
| 4,968,296 | 11/1990 | Rich et al. ............ 604/8 |

FOREIGN PATENT DOCUMENTS

| | | |
|---|---|---|
| 0137528 | 4/1985 | European Pat. Off. . |
| 0063198 | 8/1985 | European Pat. Off. . |
| 416881 | 2/1981 | Sweden . |
| 450996 | 8/1987 | Sweden . |

*Primary Examiner*—C. Fred Rosenbaum
*Assistant Examiner*—C. Maglione
*Attorney, Agent, or Firm*—Merchant, Gould, Smith, Edell, Welter & Schmidt

[57] ABSTRACT

A drainage tube (1) for drainage of sinus maxillaris consists of a middle portion (1b) having an exterior dimension adapted to a hole made in the bone wall between nasal cavity and sinus maxillaris, an extendible end portion preferably outwardly foldable legs (6) and an opposite end portion (2) widened compared with the middle portion (1b), preferably a collar. For making the hole in the bone wall is developed a tube-formed drill, which in its free end edge is formed with a toothed cutter, and for the insertion of the drainage tube in position between nasal cavity and sinus maxillaris is developed a particular insertion instrument.

2 Claims, 1 Drawing Sheet

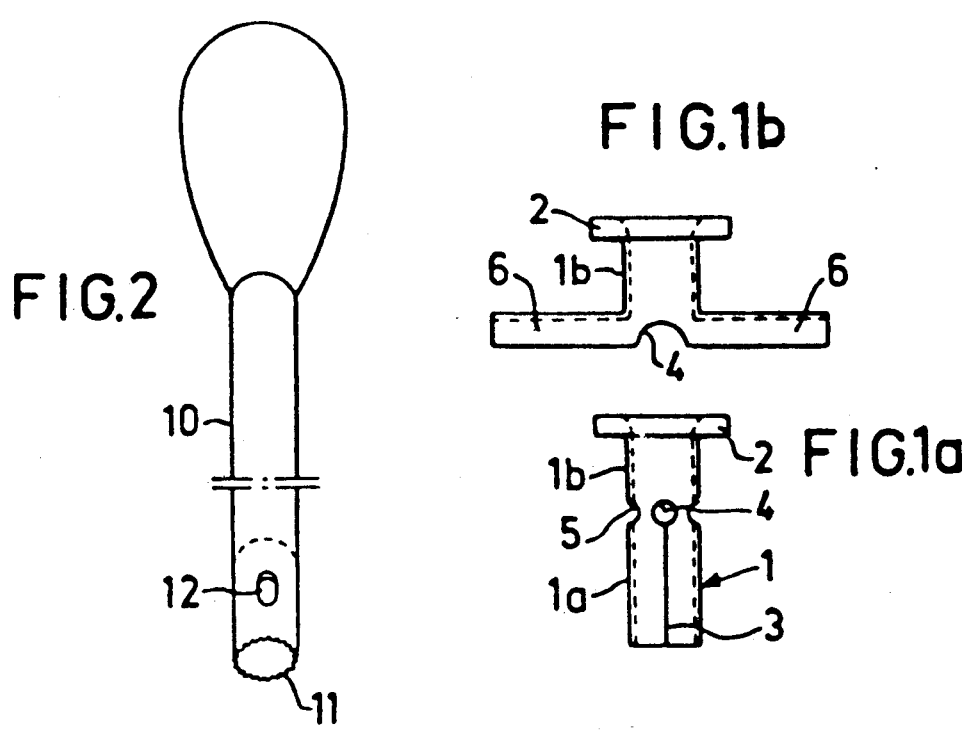
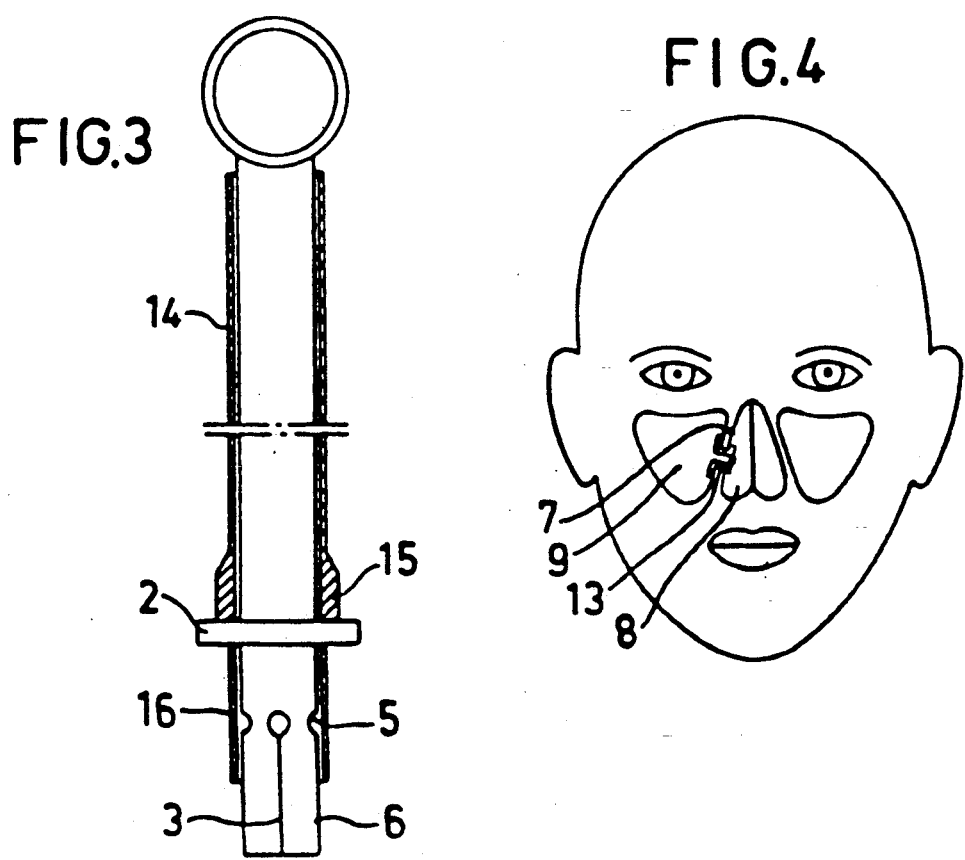

DRAINAGE TUBE FOR SINUS MAXILLARIS, A MEANS FOR ITS INSERTION AND A MEANS FOR MAKING A HOLE FOR ITS POSITIONING

BACKGROUND OF THE INVENTION

The present invention relates to a drainage tube for creating permanent access to sinus maxillaris during a desired length of time, particularly for drainage of the sinus maxillaris. Sinus maxillaris is often alone or in combination with other paranasal sinuses a seat for infections resulting in suppuration collection with accompanying pain, soreness and weight feeling. The treatment of such infections is firstly directed to drainage of the suppuration collection through puncture of the sinus maxillaris and sucking-out of the suppuration and/or flushing thereof. This therapy must, usually in combination with medicine treatment, often be repeated several times before the infection has been removed.

Puncture and flushing of sinus maxillaris usually takes place in such a manner that after local anaesthesia of the nasal mucosa a sharp needle is inserted into the nose below the inferior coucha. The needle is forced with great force through the bone wall into the sinus maxillaris. Possibly, a portion of the suppuration is thereafter sucked out for diagnosis and bacterium culture, whereupon the remaining suppuration can be flushed out through the normal, but owing to the infection often closed, ostium of the sinus maxillaris. The above described treatment is troublesome for the patient, particularly when it must be repeated several times before the infection is healed and disappeared. Moreover, many patients have disposition for recurring infections which require accompanying new treatments. These patients stand the risk of developing chronic infections and inflammations which in the end require radical surgical evacuation of sinus maxillaris.

Summing up, the means for current treatment of acute and chronic purulent infections in sinus maxillaris are unsatisfactory for the following reasons:

1. Puncture and flushing must be often repeated.
2. Gives only temporary recovery and must almost always be combined with antibiotic treatment.
3. Does not prevent new infections.

There are also on the market some different types of drainage which, however, are all intended for short use in connection with acute infection. These drainages consist of a hose having a few millimeters in diameter, which hose with the aid of a needle is forced through the bone wall into the sinus maxillaris. The hose is applied in such a manner that it gives the possibility to flush the sinus maxillaris during some time without the need for braking up a new hole for each time. By different arrangements, the hose is prevented from falling out of sinus maxillaris.

Besides the disadvantage of only being intended for short use in connection with acute infection, these drainages with hoses have other disadvantages deriving from the manner to apply the hose, as well as from the shape and the dimension thereof.

These problems have led to the development of the present invention, and by the invention the following advantages are obtained:

1. The drainage can be applied in a manner which is almost entirely pain-free and liniant for the patient.
2. The diameter of the drainage is such that a continuous discharge of suppuration and secretions and inflow of air can take place unprevented. The drainage allows the possibility of sucking out suppuration and secretions as well as, when need arises, flushing sinus maxillaris.
3. The configuration and the application is such that the drainage can be maintained during a long time, and not only cure acute infections, but also prevent new infections by providing for continuous out-flow and circulation of air.
4. The drainage allows the insertion of fibre optical equipment.

In order to obtain the above mentioned advantages, the present invention relates to a drainage tube for the application in a hole made in the bone wall between sinus maxillaris and nasal cavity for treatment of infections in sinus maxillaris and arranged for permanent application on the bone wall during the entire treatment time before its removal by extraction. The characteristics of the drainage tube according to the invention appear from the enclosed claims.

When using a drainage tube according to the invention it is essential that the hole in the bone wall between sinus maxillaris and nasal cavity is made with correctly adapted dimension to the drainage tube and that bone wall pieces and flakes are prevented from coming into sinus maxillaris. The invention also includes a hole making instrument which, as distinguished from previously known instruments being pushed through the bone wall, consists of a drill which drills out a bone plug which is caught in the instrument and removed when the hole is finished. This drill according to the invention is pre-shaped and is in its free end, formed as a circular cutter.

Also the insertion and the application of the drainage tube are of essential importance. The invention also provides particular instrument for correct application of the drainage tube. This instrument is characterized in that it is tube-formed having an exterior dimension adapted to the dimension of the hole in the bone wall and an interior dimension adapted to the dimension of the middle portion of the drainage tube, wherein the free end portion of the instrument is formed to hold the extensible end portion of the drainage tube in an unextended position corresponding to the dimension of the exterior dimension of the middle portion and having a part of this end portion projecting out of the free end of said end portion of the instrument. The instrument is provided with support means for abutting the surface of the collar-like end portion of the drainage tube being faced away from the extensible end portion.

BRIEF DESCRIPTION OF THE DRAWINGS

Embodiments of the invention are in the following described more in detail with reference to the accompanying drawings, in which FIGS. 1a, b are side views showing a drainage tube according to the invention in two different positions, FIG. 2 is a perspective view of a hole making instrument appropriate to use in connection with the drainage tube, FIG. 3 shows an instrument for the insertion of the drainage tube, and FIG. 4 illustrates a drainage tube positioned in situ between sinus maxillaris and nasal cavity.

DESCRIPTION OF THE INVENTION

The drainage tube 1 shown in FIG. 1 is at one end provided with a collar 2 and out from the opposite end provided with a slit 3 ending in a hole 4. Level with the hole 4, the drainage tube is formed with opposite recesses 5. By this form and by using an appropriate material, the drainage tube consists of an extensible portion 1a below the recesses 5, which portion in released position automatically takes the position with outwardly projecting legs 6 as shown in Fig. 1b, a middle portion 1b, and an extended portion at the opposite end, i.e. the collar 2.

For the application of the drainage tube 1 through the bone wall 7 between nasal cavity 8 and sinus maxillaris 9 (see FIG. 4) a particular hole making instrument has been developed. This instrument is shown in FIG. 2 and consists of a drill 10 tube-formed, at least at the end, and provided with a circular cutter 11 having a toothed edge. When making a hole in the bone wall 7, a bone plug is drilled out. The bone plug is picked-up within the drill tube and is removed together with the drill. It is hereby secured that bone pieces or flakes do not fall into sinus maxillaris 9. After removing the drill, the bone plug can be removed from the drill through hole 12.

For the positioning of the drainage tube 1 in a hole 13 in the bone wall 7 (FIG. 4) made by the drill 10, a particular instrument is developed which in an embodiment is shown in FIG. 3. The instrument consists of a tube 14 having an extended portion 15 for abutment against the collar 2. The tube 14 extends with a free end portion 16 through the hole of the collar 2 and past the recesses 5 of the drainage tube for holding the legs 6 abutting each other. When the instrument is removed, the legs 6 project outwardly within sinus maxillaris 9, while the collar 2 is positioned in the nasal cavity 8, whereby the drainage tube 1 becomes fixed.

The drainage tube according to the invention is adapted for both permanent and short-time use. It is made of tissue friendly and durable material. If the material is a material with radiographic opacity it can preferably be provided with a radiographic opacity marking.

The treatment of a patient and a handling of the invention can take place in the following manner. After appropriate anaesthesia of the nasal mucosa, a hole is made between nasal cavity and sinus maxillaris with the aid of the hole making instrument 10. Due to its form, no bone pieces or flakes enter sinus maxillaris 9. The cut-out bone plug is removed together with the instrument and the hole 13 becomes exactly defined in size. With the aid of the insertion instrument 14, the drainage tube 1 with the legs 6 abutting each other is moved through the hole 13 until the collar 2 abuts the bone wall 7. Thereafter, the insertion instrument is removed and the legs 6 automatically fold outwardly. Through the hole in the drainage tube 1 suppuration and secretions can freely flow out into the nasal cavity 8 and air can pass from the nose into sinus maxillaris 9. Suppuration can furthermore be sucked out through the drainage tube. A hose can be inserted through the drainage tube and the sinus maxillaris can be flushed, when required. Moreover, an instrument for fibre optical searching can be inserted through the drainage tube or the hole. When removing the drainage tube after a desired time, the collar 2 can be grasped by tongs and the drainage tube can be withdrawn straight and outwardly. Due to the flexible soft structure of the drainage tube, the legs 6 are drawn together when passing through the hole 13 in the bone wall 7.

The invention is not limited to the embodiments described above and shown on the drawings, but can be varied in several ways within the frame of the following claims. Thus, the extendable portion of the drainage tube can for instance be shaped in another way as well as the extended portion collar. Moreover, the insertion instrument can be shaped in another way for the adaptation to the form of the drainage tube.

We claim:

1. An apparatus for treatment of infections in a sinus maxillaris including:
   a drainage tube adapted to be positioned in a hole made in a wall between a nasal cavity and the sinus maxillaris and arranged for permanent positioning in the wall during an entire treatment time before its removal by extraction, the drainage tube comprising:
      a middle portion having an exterior dimension closely adapted to the dimension of the hole and having an interior dimension sufficiently large for guaranteeing continuous flow of suppuration and secretions as well as gas exchange through the drainage tube,
      an extendible end portion extending from the middle portion and automatically extendable to a larger dimension than the middle portion to be arranged in the sinus maxillaris, and
      a collar-like end portion extending from the middle portion opposite the extendible end portion and having a dimension larger than the middle portion to be arranged in the nasal cavity, wherein the length of said middle portion is sized for substantially fixed arrangement of the drainage tube at the wall due to the close adaptment of the middle portion thickness to the wall thickness, the extendible end portion and collar-like end portion abutting against surfaces around said hole, the extendible end portion abutting the side of the wall of the sinus maxillaris and the collar-like end portion abutting the side of the wall in the nasal cavity; and
   means for inserting the drainage tube in the wall between the nasal cavity and the sinus maxillaris, the means for inserting being tube-formed and having a free end portion and an exterior dimension substantially corresponding to the dimension of the hole in the wall and an interior dimension substantially corresponding to the exterior dimension of the middle portion of the drainage tube, the free end portion being formed to hold the extendible end portion of the drainage tube in a nonextended position corresponding in dimension to the outer dimension of the middle portion and with a part of said extendible end portion projecting out of the free end portion, the means for inserting being provided with support means for abutment against the surface of the collar-like end portion of the drainage tube faced away from the extendible end portion.

2. An apparatus for treatment of infections in a sinus maxillaris including:
   a drainage tube adapted to be positioned in a hole made in a wall between a nasal cavity and the sinus maxillaris and arranged for permanent positioning in the wall during an entire treatment time before its removal by extraction, the drainage tube comprising:
      a middle portion having an exterior dimension closely adapted to the dimension of the hole and having an interior dimension sufficiently large for guaranteeing continuous flow of suppuration and secretions as well as gas exchange through the drainage tube, an extendible end portion extending from the middle portion and automatically extendable to a larger dimension than the middle portion to be arranged in the sinus maxillaris, and a collar-like portion extending from the middle portion opposite the extendible end portion and having a dimension larger than the middle portion to be arranged in the nasal cavity, wherein the length of said middle portion is sized for substantially fixed arrangement of the drainage tube at the wall due to the close adaptment of the middle portion thickness to the wall thickness, the extendible end portion and collar-like end portion abutting against surfaces around said hole, the extendible end portion abutting the side of the wall of the sinus maxillaris and the collar-like end portion abutting the side of the wall in the nasal cavity; and means for making a hole in the wall between a nasal cavity and the sinus maxillaris for positioning of the drainage tube, the means for making comprising a tube-formed drill having a free end edge at one end of said drill, the free end edge being formed as a circular cutter.

* * * * *